(12) United States Patent
Bennett et al.

(10) Patent No.: US 11,320,363 B2
(45) Date of Patent: May 3, 2022

(54) TREATMENT OF PIPELINE DEPOSITS

(71) Applicant: Halliburton Energy Services, Inc., Houston, TX (US)

(72) Inventors: David Bennett, Conroe, TX (US); Bo Gentry, Houston, TX (US); Philippe Prince, Pearland, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 256 days.

(21) Appl. No.: 16/559,538

(22) Filed: Sep. 3, 2019

(65) Prior Publication Data
US 2021/0063300 A1 Mar. 4, 2021

(51) Int. Cl.
| | |
|---|---|
| *C09K 8/524* | (2006.01) |
| *G01N 17/00* | (2006.01) |
| *G06Q 10/06* | (2012.01) |
| *B08B 3/08* | (2006.01) |
| *C09K 8/52* | (2006.01) |
| *G06Q 50/02* | (2012.01) |

(52) U.S. Cl.
CPC ............. *G01N 17/008* (2013.01); *B08B 3/08* (2013.01); *C09K 8/52* (2013.01); *C09K 8/524* (2013.01); *G06Q 10/0637* (2013.01); *G06Q 10/06395* (2013.01); *G06Q 50/02* (2013.01); *C09K 2208/22* (2013.01)

(58) Field of Classification Search
CPC ........ G01N 17/008; B08B 3/08; C09K 8/524; C09K 8/52; C09K 2208/22; G06Q 10/06395; G06Q 50/02; E21B 36/13
See application file for complete search history.

(56) References Cited

U.S. PATENT DOCUMENTS

| | | | |
|---|---|---|---|
| 5,827,952 A | 10/1998 | Mansure et al. | |
| 6,311,549 B1 * | 11/2001 | Thundat | G01N 9/002 |
| | | | 73/24.05 |
| 6,467,340 B1 | 10/2002 | Gallagher | |
| 6,701,787 B2 | 3/2004 | Han et al. | |
| 6,993,963 B1 | 2/2006 | Gudmundsson | |
| 7,069,786 B2 * | 7/2006 | Dunhill | B06B 1/06 |
| | | | 310/327 |
| 7,308,941 B2 | 12/2007 | Rolovic et al. | |
| 8,487,776 B2 | 7/2013 | Livchak et al. | |
| 9,291,019 B2 | 3/2016 | Aphale et al. | |

(Continued)

FOREIGN PATENT DOCUMENTS

WO 03-031950 4/2003

OTHER PUBLICATIONS

Paraffin Deposition and Prevention in Oil Wells, Jorda, Dec. 1966.
(Continued)

*Primary Examiner* — Silvana C Runyan
(74) *Attorney, Agent, or Firm* — Tenley Krueger; C. Tumey Law Group PLLC

(57) ABSTRACT

A method may include: generating a signal in a conduit; measuring the signal; generating data representing a deposit in the conduit, the data being generated by a deposition identification model, wherein the deposition identification model utilizes the signal as an input; generating a treatment plan based at least in part on the data representing the deposit; and applying a chemical additive to the conduit based at least in part on the treatment plan.

19 Claims, 3 Drawing Sheets

(56) References Cited

U.S. PATENT DOCUMENTS

2009/0145661 A1 6/2009 Jeffryes et al.
2013/0276250 A1 10/2013 Yang et al.
2017/0058185 A1* 3/2017 Naumov ............... C09K 8/524

OTHER PUBLICATIONS

Sanjay, M., Simanta, B., & Kulwant, S. (1995). Paraffin Problems in Crude Oil Production And Transportation: A Review. SPE Production & Facilities, 10(01), 50-54.
Measuring Asphaltenes and Resins, and DipoleMoment in Petroleum Fluids, Gougal 2002.
Modeling Asphaltene Phase Behavior in Crude Oil Systems Usingthe Perturbed Chain Form of the Statistical Associating FluidTheory (PC-SAFT) Equation of State, Vargas et al Aug. 15, 2008.
Remediation of Asphaltene and other Heavy Organic Deposits in Oil Wells and in Pipelines, Mansoori Apr. 2010.
Sheikh Mohammad Samiur, R., & Chacko, S. (2013). Improved Paraffin-Deposition-Profile Estimation in Hydrocarbon Pipelines and Effective Mitigation Review. Oil and Gas Facilities, 2(06), 78-85.
Hart, A. (2013). A review of technologies for transporting heavy crude oil and bitumen via pipelines. Journal of Petroleum Exploration and Production Technology, 4(3), 327-336.
S. Askarova, G. Boyko, et al., Complex reagents for the removal and inhibition of paraffin deposition for highly paraffinic oil production and transportation WIT Transactions on Ecology and The Environment, vol. 186, © 2014 WIT Press.
Jalalnezhad, M. J., & Kamali, V. (2015). Development of an intelligent model for wax deposition in oil pipeline. Journal of Petroleum Exploration and Production Technology, 6(1), 129-133.
Quan, Q., Wang, W., Wang, P., Yang, J., Gao, G., Yang, L., & Gong, J. (2016). Effect of Oil Temperature on the Wax Deposition of Crude Oil With Composition Analysis. Brazilian Journal of Chemical Engineering, 33(4), 1055-1061.
Mohamed Ben Mahmoud, Abdulrauf. A. Aboujadeed, Compatibility Assessment of Crude Oil Blends using Different Methods, Chemical Engineering Transactions, vol. 57, 2017.
Vladimir Yurievich Koptev and Alexandra Vladimirovna Kopteva, Improving Paraffin Deposits Detection Methodology for Better Ecological Safety during Hydrocarbon Transportation, vol. 12, No. 5 pp. 618-621, 2017.
International Search Report and Written Opinion for Application No. PCT/US2019/049537, dated Jun. 2, 2020.

* cited by examiner

TREATMENT OF PIPELINE DEPOSITS

BACKGROUND

During oil exploration, production, transportation, refining, and chemical processing, surfaces may become contaminated with deposits from crude oils. Some chemical species such as asphaltenes, paraffins, and mineral scales, for example, may be naturally present in crude oils. These chemical species, among others, may deposit on surfaces such as tubulars in the case of oil exploration, or on surfaces of pipelines during oil transport. Pipeline depositions have been known and studied since the early 1920's and there have been many methods developed to treat pipeline depositions. Despite the range of treatment programs and methods, well failures and pipeline dockages due to deposition still occur.

Paraffins are long chain hydrocarbons which may vary in consistency from jelly-like to hard wax. When oil and gas is produced from a relatively hotter formation and transported into relatively cooler equipment such as tubulars, paraffins present may begin to crystalize and separate from the bulk hydrocarbon phase and deposit on surfaces. Paraffins may be relatively insoluble in oil and gas at temperatures lower than formation temperatures and thus hydrocarbons flowing in tubulars containing paraffin deposits generally will not dissolve the paraffin deposits. The composition of petroleum produced from a well, whether by conventional methods or unconventional methods, may change over time and thus the amount of deposition and rate thereof also varies over time. The amount and rate of deposition from oil and gas may vary based on the oil or gas composition and environmental production factors, for example.

Current industry practices to determine deposition and fallout rates and subsequent treatment programs require sampling at regular intervals and laboratory testing of samples. There is a lag time between the sampling time and laboratory testing and thus treatment programs developed may lag the actual composition of petroleum being produced or transported. Furthermore, treatments are typically not adjusted until a noticeable production drop off or well failure is observed resulting in potential revenue and production losses.

BRIEF DESCRIPTION OF THE DRAWINGS

These drawings illustrate certain aspects of some of the present disclosure and should not be used to limit or define the disclosure.

DETAILED DESCRIPTION

The embodiments described herein may relate to deposition management and, more particularly, may relate to configuration and integration of a non-intrusive detection and treatment method for asphaltene, paraffin, hydrate, and scale buildup on wellbore equipment and pipeline surfaces. In one or more embodiments, the methods may relate to detection of asphaltene, paraffin, and scale buildup and automated treatment adjustments to address detected issues. The methods disclosed herein may be performed without impeding fluid flow while enabling short response times for remediation recommendations.

Figure 1:
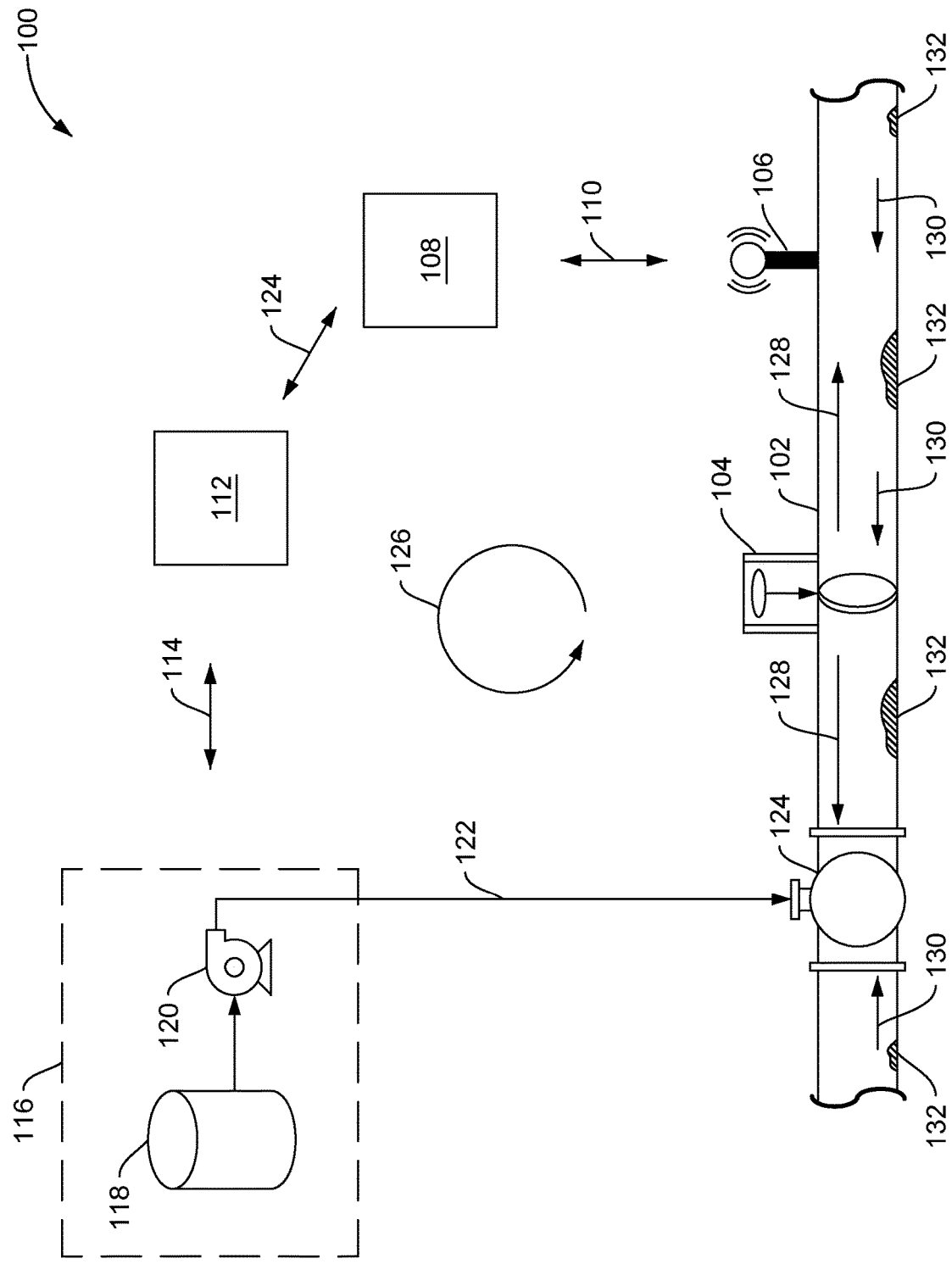
FIG. 1 illustrates a non-intrusive deposition management system.

FIG. 1 illustrates a non-intrusive deposition management system 100. Although non-intrusive deposition management system 100 is shown in FIG. 1 as being part of a pipeline 102, non-intrusive deposition management system 100 may alternatively, or in addition to, be disposed on a producing wellbore. Pipeline 102 may be fluidically connected to a source of hydrocarbons such as a producing well or hydrocarbon storage area such as a tank farm or other hydrocarbon storage media. Pipeline 102 may include a signal generator 104 disposed on or within pipeline 102. Signal generator 104 may be operable to produce an acoustical or pressure signal 128 within pipeline 102 which may propagate through pipeline 102. Acoustical or pressure signal 128 may interact with deposits 132 which may alter acoustical or pressure signal 128 by altering the amplitude, phase, frequency, or any combination thereof of acoustical or pressure signal 128. In smooth conduits with no deposits, returning signals such as reflected signals may be relatively unchanged. Conversely, when deposits are present, returning signals may exhibit additional characteristics different from the generated signal. Friction factors associated with deposits may determine how and to what degree acoustical or pressure signal 128 is altered when encountering deposits 132. Reflected signals may be used to determine the location and magnitude of a deposit, for example.

A signal receiver 106 may be disposed on or within pipeline 102 at an upstream or downstream location from signal generator 104. Signal receiver 106 may be operable to detect acoustical or pressure signal 128 produced by signal generator 104 or returning signals 130. Returning signals 130 may be reflected acoustical or pressure waves reflected by deposits 132 or other features within pipeline 102. Signals collected by signal receiver 106 may be converted to a data file or data stream and transmitted to signal analysis unit 108 via transmission 110. Transmission 110 may be wired or wireless, for example. A deposition analysis may be conducted by signal analysis unit 108. Deposition analysis may include calculating a location and amount of deposition, for example. Deposition analysis may further include chemical identification of deposits which may be performed by analyzing historical deposition trends, by chemical analysis of hydrocarbons within pipeline 102, by historical chemical analysis of hydrocarbons within pipeline 102, and external environmental data as well as analysis of the transmitted acoustical or pressure signal. amount of deposition. Acoustical and pressure wave generator and recorders enable monitoring of acoustical or pressure variations in a pipeline or wellbore. One of ordinary skill, with the benefit of this disclosure, would understand how to analyze collected data from acoustical or pressure recorders and apply an algorithm to identify the deposit. The algorithm may give information such as the chemical identity, quantity, and location of the deposit for example. Analysis and calculating trends of deposit volumes may include incorporating parameters such as oil or gas composition, time, environmental conditions, treatment plans, and previous deposition levels, for example.

Signal generator 104 may be any suitable signal generator configured to be operable to generate a pressure wave or an acoustic wave through pipeline 102. Signal generator 104 may include a diaphragm, a fast-closing valve capable of generating a detectable pressure signal, linear-actuator, electroacoustic transducers, or any combinations thereof, for example. The signal generator 104 may produce a recognized acoustical or pressure signal generated within a defined timeframe such that a distortion in the acoustical or pressure signal may be used in support of deposition calculations. Signal receiver 106 may include any suitable receiver operable to detect the signal generated from signal generator 104. Signal receiver 106 may include a transducer configured to detect the signal generated by signal generator 104 and generate an output electrical signal. Some examples of signal generator 104 may include a pressure transducer or hydrophone, for example.

Signal analysis unit 108 may communicate the results of the deposition analysis to treatment analysis unit 112 via transmission 124. In some examples, signal analysis unit 108 and treatment analysis unit 112 may be an integrated unit. Treatment analysis unit 112 may interpret results of the deposition analysis performed by signal analysis unit 108 and calculate a treatment regimen and schedule tailored to address the type and amount of deposit. The treatment regimen may include the type of chemical additive and amount thereof to treat the deposit, for example. The treatment regimen may be based at least in part on deposition analysis, compositional analysis of the hydrocarbon within pipeline 102, elapsed time, environmental conditions, previous treatment plans, treatment results, or any combinations thereof, for example. In some examples, depositions may be continuously monitored, and a treatment regimen may be continuously adjusted to account for deposits in real time.

In the instance of paraffin wax deposits, the chemical additive may include, but is not limited to, solvents, wax crystal modifiers, dispersants, surfactants, or any combination thereof. For other identified deposits, the chemical additive may be selected that are effective in treating the deposit. Treatment regimen and schedules may be transmitted to an operator for review before implementation or the implementation may be automatic. Transmission 114 represents the treatment regimen and schedule being transmitted to a treatment unit 116 which may include treatment tank 118 including chemical treatment species, a pump 120, and control systems operable to implement the treatment regimen and schedule from treatment analysis unit 112. In accordance with the treatment regimen, the amount and type of chemical additive may be adjusted by, for example, adjusting pump rates within treatment unit 116. Treatment fluid 122 may be added to pipeline 102 via treatment point 124, for example. Arrow 126 is representative that the process described above may be performed continuously such that deposition monitoring and treatment may be monitored and adjusted in real time to ensure pipeline performance.

Figure 2:
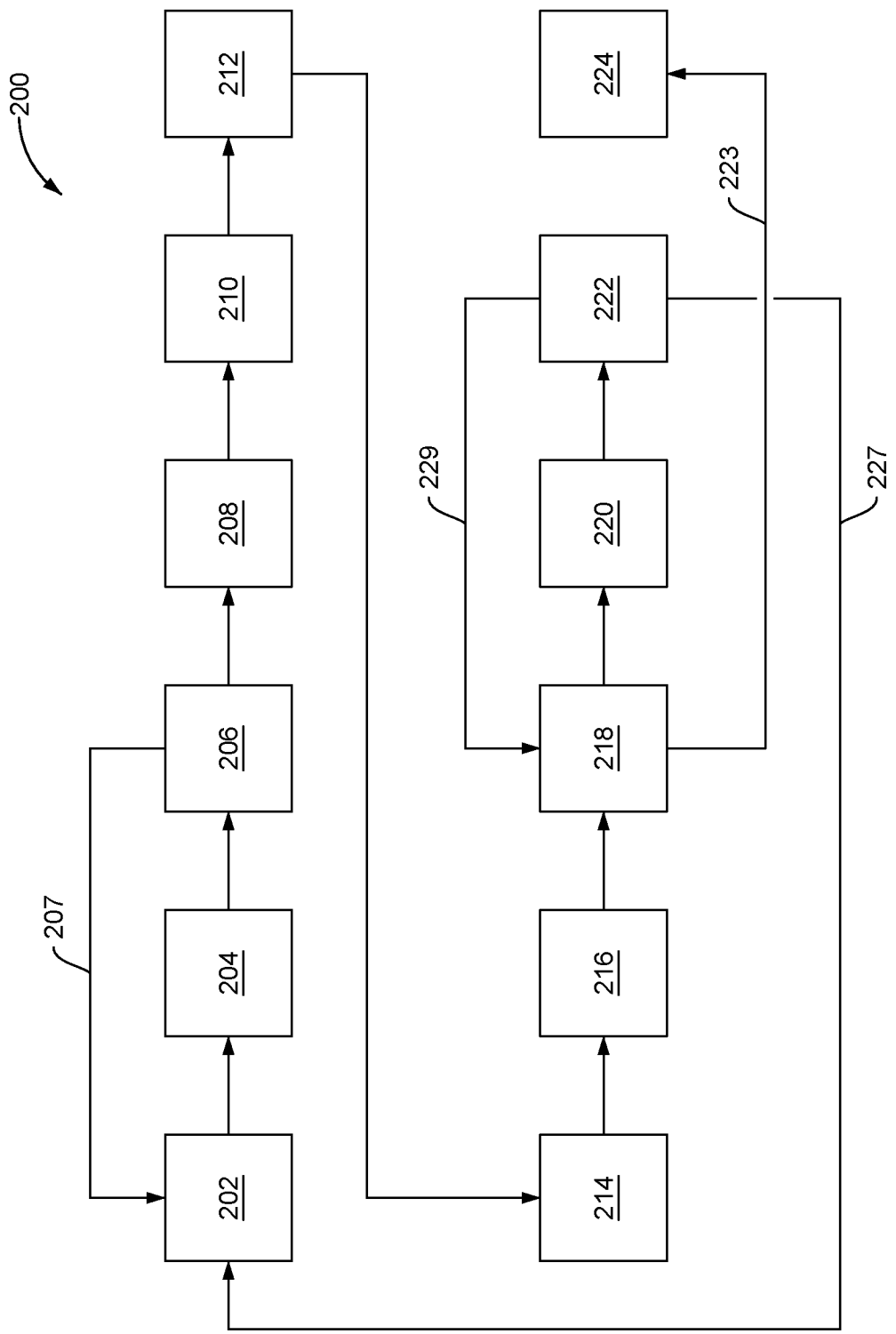
FIG. 2 illustrates a non-intrusive deposition management method.

FIG. 2 illustrates a non-intrusive deposition management method 200. Method 200 may begin at block 202 where a signal may be generated. Block 202 may correspond to signal generator 104 of FIG. 1 propagating an acoustical or pressure signal through a pipeline or wellbore. An acoustical or pressure signal may be generated by a control system on an automated basis or may be initiated by a user. In some example, a combination of acoustical and pressure signals may be generated in block 202. In block 204, the signal generated in block 202 may be received by a signal receiver and a digital file representing the received signal may be generated. In some example, block 204 may utilize a signal receiver such as signal receiver 106 of FIG. 1. However multiple receivers may also be used which may provide improved results over a single receiver. only one signal source and receiver as illustrated in FIG. 1, there may be multiple signal receivers at block 206 the file generated in block 204 may be validated to ensure the quality of the received signals. File validation may be accomplished by verifying signal to noise ratio for example. Arrow 207 indicates the file quality being below a threshold and the method returning to block 202 to generate another signal. At block 208 the file may be pre-processed before transmission in block 210. Pre-processing in block 208 may prepare the file for transmission by compressing the file, for example. In block 210, transmission may be any kind of file transmission including over a wired or wireless connection to an intranet or internet connection, for example.

In block 212, the transmission from block 210 may be received by a signal analysis unit such as signal analysis unit 108 illustrated in FIG. 1. In block 212, the received file and digital representation of collected signals therein, may be processed according to deposition identification methods well known in the art. A deposition identification method may include using a deposition identification model to be able to determine material quantity, location, and chemical identity of deposits. A deposition identification model may take signals from the received file as input and utilize model parameters such as acoustic velocity, viscosity, and density, for example to calculate a model output including the material quantity, location, and chemical identity of deposits. In block 214, calibration analysis may be performed to confirm model parameters used in block 212. For example, a calibration may be performed based on known intervals between the point of signal generation in block 202 and signal receiving in block 204. Calibration may confirm acoustic velocity (speed of sound) in the pipeline or wellbore as well as viscosity and density of fluids in the pipeline or wellbore. The calibration steps may be used to adjust the results of block 212. In some examples, a calibration calculation may be performed before calculating the deposition identification model. Additional processing may also occur in block 214 such as comparing the calculated from block 212 to historical deposits, comparing the calculated deposits to deposition trends, and performing a regression analysis on calculated deposits, for example. Historical deposition data may be used as an input to regression scheme to generate a historical deposition model.

One objective of treating a conduit containing deposits may be to treat existing deposits and prevent further deposits from forming. Developing a treatment schedule and regimen for existing deposits may be accomplished by analyzing the results of block 212 and 214 and selecting a chemical or physical treatment that is effective at removing the deposits. Preventing depositions from forming may require analysis of the constituent components of the oil and/or gas as oil or gas may include components that deposit on surfaces at different rates under different conditions. The rate of deposition by a particular component may be affected by environmental factors such as fluid velocity and temperature as well as well as the chemical identity of the component. A rate of deposition may be modeled using a deposition model as is known in the art. The deposition model may take as input the chemical identity and concentrations thereof of components of the oil and gas may use deposition model parameters including environmental factors and output a rate of deposition, for example. An output of the deposition model may allow prediction of the amount and identity of deposition within a pipeline or wellbore as a function of time. In some examples, the deposition model may be a regression model.

In block 216, model parameters may be subjected to integrated attribute analysis. One exemplary integrated attribute analysis may include environmental analysis, such as weather characteristics and temperature measurement.

Ambient temperature may affect temperature within a pipeline or wellbore. Ambient temperature predictions may be used to estimate cooling rates or heating rates over time. Another integrated attribute analysis may include fluid characteristics such as chemical assays and analysis of the oil and gas. Chemical assays may be performed in real-time such as with an inline chemical sensor that may output chemical compositions or may be performed in batch assays by laboratory testing, for example. Another integrated attribute analysis may include deposition characteristic analysis. Chemical assays and deposition measurements may be reviewed to support confirmation of deposition compositions and guide treatment recommendations. Results from each of the integrated attribute analyses may be included in the deposition model which may further increase a confidence level of deposition model results. An output from block 216 may be predicted future deposit amounts.

In block 218, a treatment plan may be developed based at least in part on existing deposits calculated from block 214 and predicted future deposits from block 216. A treatment plan may be developed that tailors remediation efforts to the type of deposit that may be encountered. For example, deposits such as asphaltenes, paraffins, scales, and hydrates may require different treatment plans owing to the differing chemical nature of each deposit. The treatment plan may also be developed based on results from previous deposition studies. For example, trending and regression models bay be analyzed to establish expected buildup of deposits which like environmental, compositional, and fluid conditions. The treatment plan may also be developed based at least in part on well maturity. The composition fluids produced from a well may change over time as the formation is drained of fluids. Compositions of produced fluids over time may be tracked and modeled such that fluids produced from similar formations or wells in the same region may be predicted. Forecasts of expected asphaltene, paraffin, scale, and hydrate content of produced fluids based on well age may be used in the development of a treatment plan. Treatment plans may call for no change in treatment to be implemented, continuous deposition treatment to be increased, continuous deposition treatment to be decreased, direct/injected deposition treatments be increased, or direct/injected deposition treatments be decreased, for example. The treatment plan may be reviewed and validated and transmitted to application in the field either manually or automatically, depending on capabilities of field equipment. Arrow 223 illustrates the treatment plan being sent from block 218 to block 224. In block 224, pumping rates of chemical additives may be modulated according to the treatment plan formulated in block 218.

In block 220, the treatment plan may be updated using the techniques described in relation to block 118 as data about the treatment plan effectiveness is gathered. In block 222, effectiveness analysis may be performed to determine if the treatment plan is effective in reducing deposits. Arrow 227 represents a signal to block 202 to start a signal generation process to gather additional data about deposits. In this manner the time-dependent location, amounts, and identity of deposits may be tracked to adjust the treatment process. Arrow 225 represents additional data being supplied to block 218 to adjust the treatment plan as the treatment effectiveness is observed. In block 222 analysis reports may be generated for treatment effectiveness. Effectiveness may be measured by pipeline or wellbore volumetric flow rate potential versus observed volumetric flow rate, for example. Other reports may be generated such as treatment variations with respect to time and treatment effectiveness over time, for example.

Figure 3:
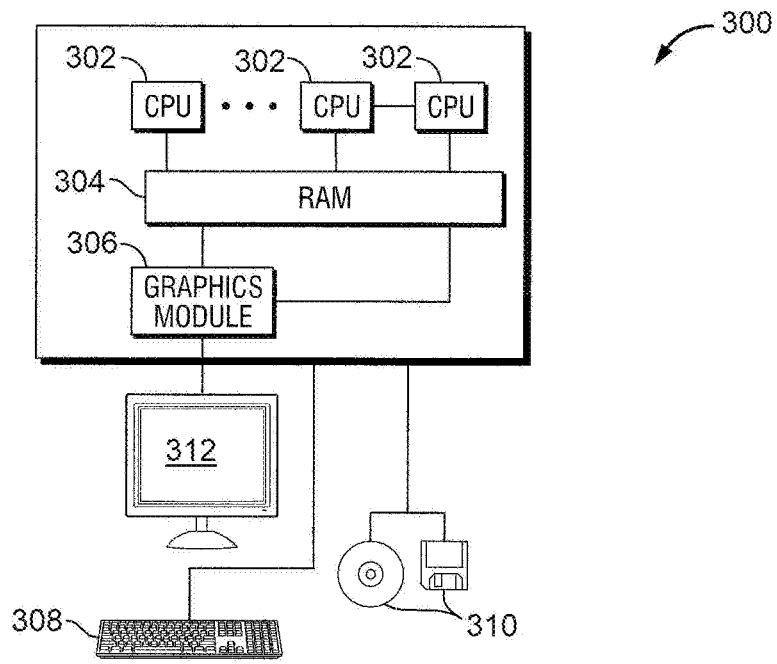
FIG. 3 illustrates an example of an information handling system.

The methods described herein may be executed using a computer or other information handling system, for example. A computer may run computer software containing instructions which configure a processor to be operable to perform a series of computations. A computer may take as an input a data file representing acoustical or pressure data, such as transmission 110, illustrated in FIG. 1. The software may contain instructions to apply a deposit identification methodology using the acoustical or pressure data contained in the data file to generate data representing a deposit in a wellbore or pipeline. The software may contain further instructions to generate a treatment plan as described above, the treatment plan being based at least in part on the data representing the deposit, for example. The software may also contain instructions to FIG. 3 generally illustrates an example of an information handling system 300 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. For example, an information handling system 300 may be a personal computer, a network storage device, or any other suitable device and may vary in size, shape, performance, functionality, and price. In examples, information handling system 300 may be referred to as a supercomputer or a graphics supercomputer.

As illustrated, information handling system 300 may include one or more central processing units (CPU) or processors 302. Information handling system 300 may also include a random-access memory (RAM) 304 that may be accessed by processors 302. It should be noted information handling system 300 may further include hardware or software logic, ROM, and/or any other type of nonvolatile memory. Information handling system 300 may include one or more graphics modules 306 that may access RAM 304. Graphics modules 306 may execute the functions carried out by a Graphics Processing Module (not illustrated), using hardware (such as specialized graphics processors) or a combination of hardware and software. A user input device 308 may allow a user to control and input information to information handling system 300. Additional components of the information handling system 300 may include one or more disk drives, output devices 312, such as a video display, and one or more network ports for communication with external devices as well as a user input device 308 (e.g., keyboard, mouse, etc.). Information handling system 300 may also include one or more buses operable to transmit communications between the various hardware components.

Alternatively, systems and methods of the present disclosure may be implemented, at least in part, with non-transitory computer-readable media. Non-transitory computer-readable media may include any instrumentality or aggregation of instrumentalities that may retain data and/or instructions for a period of time. Non-transitory computer-readable media may include, for example, storage media 310 such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

Figure 4:
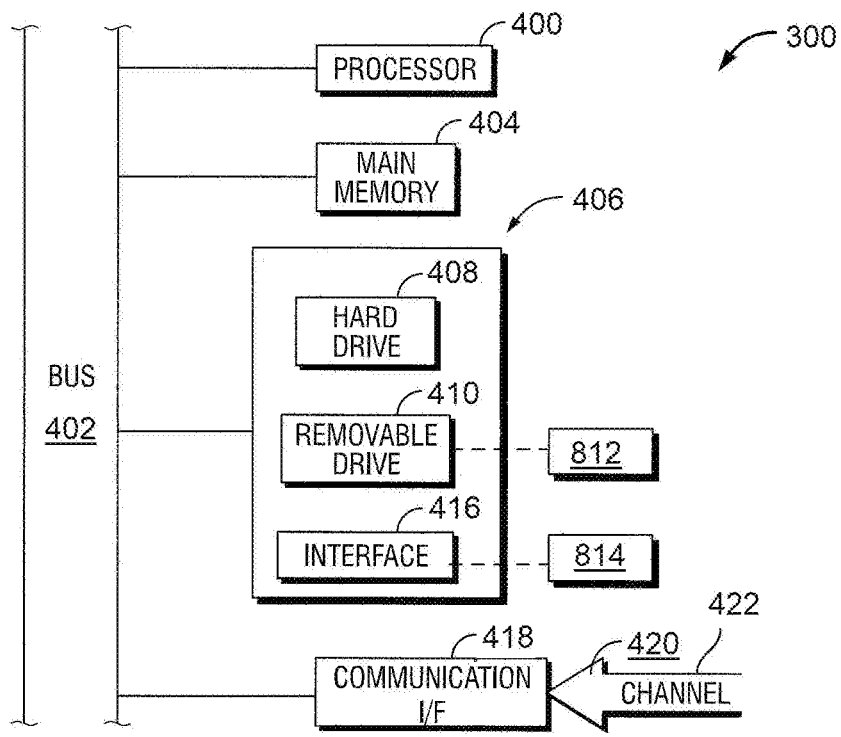
FIG. 4 illustrates additional details of an information handling system

FIG. 4 illustrates additional detail of information handling system 300. For example, information handling system 300 may include one or more processors, such as processor 400. Processor 400 may be connected to a communication bus 402. Various software embodiments are described in terms of this exemplary computer system. After reading this description, it will become apparent to a person skilled in the relevant art how to implement the example embodiments using other computer systems and/or computer architectures.

Information handling system 300 may also include a main memory 404, preferably random-access memory (RAM), and may also include a secondary memory 406. Secondary memory 406 may include, for example, a hard disk drive 408 and/or a removable storage drive 410, representing a floppy disk drive, a magnetic tape drive, an optical disk drive, etc. Removable storage drive 410 may read from and/or writes to a removable storage unit 412 in any suitable manner. Removable storage unit 412, represents a floppy disk, magnetic tape, optical disk, etc. which is read by and written to by removable storage drive 410. As will be appreciated, removable storage unit 412 includes a computer usable storage medium having stored therein computer software and/or data.

In alternative embodiments, secondary memory 406 may include other operations for allowing computer programs or other instructions to be loaded into information handling system 300. For example, a removable storage unit 414 and an interface 416. Examples of such may include a program cartridge and cartridge interface (such as that found in video game devices), a removable memory chip (such as an EPROM, or PROM) and associated socket, and other removable storage units 414 and interfaces 416 which may allow software and data to be transferred from removable storage unit 414 to information handling system 300.

In examples, information handling system 300 may also include a communications interface 418. Communications interface 418 may allow software and data to be transferred between information handling system 300 and external devices. Examples of communications interface 418 may include a modem, a network interface (such as an Ethernet card), a communications port, a PCMCIA slot and card, etc. Software and data transferred via communications interface 418 are in the form of signals 420 that may be electronic, electromagnetic, optical or other signals capable of being received by communications interface 418. Signals 420 may be provided to communications interface via a channel 422. Channel 422 carries signals 420 and may be implemented using wire or cable, fiber optics, a phone line, a cellular phone link, an RF link and/or any other suitable communications channels. For example, information handling system 300 includes at least one memory 404 operable to store computer-executable instructions, at least one communications interface 402, 418 to access the at least one memory 404; and at least one processor 400 configured to access the at least one memory 904 via the at least one communications interface 402, 418 and execute computer-executable instructions.

In this document, the terms "computer program medium" and "computer usable medium" are used to generally refer to media such as removable storage unit 412, a hard disk installed in hard disk drive 408, and signals 420. These computer program products may provide software to computer system 300.

Computer programs (also called computer control logic) may be stored in main memory 404 and/or secondary memory 406. Computer programs may also be received via communications interface 418. Such computer programs, when executed, enable information handling system 300 to perform the features of the example embodiments as discussed herein. In particular, the computer programs, when executed, enable processor 400 to perform the features of the example embodiments. Accordingly, such computer programs represent controllers of information handling system 300.

In examples with software implementation, the software may be stored in a computer program product and loaded into information handling system 300 using removable storage drive 410, hard disk drive 408 or communications interface 418. The control logic (software), when executed by processor 400, causes processor 400 to perform the functions of the example embodiments as described herein.

In examples with hardware implementation, hardware components such as application specific integrated circuits (ASICs). Implementation of such a hardware state machine so as to perform the functions described herein will be apparent to persons skilled in the relevant art(s). It should be noted that the disclosure may be implemented at least partially on both hardware and software.

The methods described herein may be carried out, at least in part, using a computer system including a computer-accessible medium, the computer-accessible medium containing a computer program that causes a processor to execute instructions that carry out at least some of the method steps described herein. In general, a computer-accessible medium may include any tangible or non-transitory storage media or memory media such as electronic, magnetic, or optical media—e.g., disk or CD/DVD-ROM coupled to the computer. The terms "tangible" and "non-transitory," as used herein, are intended to describe a computer-readable storage medium (or "memory") excluding propagating electromagnetic signals but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM), flash memory, or other volatile memory types. Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Accordingly, the present disclosure may provide methods, systems, and apparatus that may relate to configuration and integration of a non-intrusive detection and treatment method for asphaltene, paraffin, hydrate, and scale buildup. The methods, systems. and apparatus may include any of the various features disclosed herein, including one or more of the following statements.

Statement 1. A method comprising: generating a signal in a conduit; measuring the signal; generating data representing a deposit in the conduit, the data being generated by a deposition identification model, wherein the deposition identification model utilizes the signal as an input; generating a treatment plan based at least in part on the data representing the deposit; and applying a chemical additive to the conduit based at least in part on the treatment plan.

Statement 2. The method of statement 1 wherein the signal is a pressure signal, an acoustic signal, or a combination thereof and wherein the conduit is a wellbore or a pipeline.

Statement 3. The method of any of statements 1-2 wherein the step of measuring the signal comprises measuring the signal with a pressure transducer, microphone, hydrophone, or any combination thereof.

Statement 4. The method of any of statements 1-3 wherein the step of generating data representing the deposit further comprises performing a calibration calculation and using an output of the calibration calculation in the deposition identification model.

Statement 5. The method of statement 4 wherein the calibration calculation confirms at least one of acoustic velocity, viscosity, or density.

Statement 6. The method of any of statements 1-5 wherein the treatment plan comprises an identity and a flow rate of the chemical additive, the chemical additive being operable to treat the deposit.

Statement 7. The method of statement 6 wherein the deposit is at least one of asphaltene, paraffin, hydrate, or scale.

Statement 8. The method of any of statements 1-7 further comprising: performing an integrated analysis of at least one of environmental characteristics, fluid characteristics, or deposition characteristics to generate integrated analysis data; and comparing the data representing the deposit to a regression model of historical deposits to generate a historical comparison data.

Statement 9. The method of statement 8 wherein the step of generating the treatment plan is further based at least in part on the integrated analysis data and historical comparison data.

Statement 10. The method of any of statements 1-9 further comprising: determining an effectiveness of the treatment plan; and updating the treatment plan based at least in part on the effectiveness of the treatment plan.

Statement 11. The method of claim 1 wherein the step of applying the chemical additive comprises transmitting the treatment plan to a treatment unit, the treatment unit comprising a control system operable to implement the treatment plan by controlling a pump fluidically connected to the chemical additive.

Statement 12. A non-transitory computer readable medium having data stored therein representing software executable by a computer, the software including instructions comprising: instructions to accept a computer file representing acoustical or pressure signals; instructions to generate data representing a deposit, the data being generated by a deposition identification model wherein the deposition identification model utilizes the acoustical or pressure signals as an input; and instructions to generate a treatment plan based at least in part on the data representing the deposit.

Statement 13. The non-transitory computer readable medium of statement 12 wherein the instructions further comprise: instructions to perform a calibration calculation and using an output of the calibration calculation in the deposition identification model.

Statement 14. The non-transitory computer readable medium of statement 13 wherein the calibration calculation confirms at least one of acoustic velocity, viscosity, or density.

Statement 15. The non-transitory computer readable medium of any of statements 12-14 wherein the instructions to generate a treatment plan comprise: instructions select at least one chemical additive and a flow rate thereof based at least in part on the data representing the deposit.

Statement 16. The non-transitory computer readable medium of statement 15 wherein the instructions to generate a treatment plan further comprise: instructions to perform an integrated analysis of at least one of environmental characteristics, fluid characteristics, or deposition characteristics to generate integrated analysis data, wherein the instructions to select at least one chemical additive and a flow rate thereof is further based at least in part on a result of the integrated analysis.

Statement 17. The non-transitory computer readable medium of any of statements 12-16 further comprising: instructions to transmit the treatment plan to a treatment unit.

Statement 18. A system comprising: an acoustical or pressure signal generator configured to generate an acoustical or pressure signal; an acoustical or pressure signal receiver configured to receive the acoustical or pressure signal and generate a signal output; a signal analysis unit configured to accept the signal output and generate data representing a deposit; a treatment analysis unit configured to accept the data representing the deposit as an input and generate a treatment plan, the treatment plan comprising at least one chemical additive and a flow rate thereof; and a treatment unit configured to accept the treatment plan as an input.

Statement 19. The system of statement 18 wherein the treatment analysis unit configured to generate the treatment plan based at least in part on historical deposition trends, an integrated analysis of environmental characteristics, fluid characteristics, or deposition characteristics, and the data representing the deposit.

Statement 20. The system of any of statements 18-19 wherein the treatment unit comprises: a pump fluidically coupled to the chemical additive; and a control system operable to control the pump, wherein the control system is configured to accept the treatment plan as an input and control the pump based at least in part on the treatment plan.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The claims are not intended to be limited to the aspects described herein but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A method comprising:
   generating a signal comprising a pressure signal, an acoustic signal, or a combination thereof in a conduit comprising a pipeline;
   measuring the signal;
   generating data representing a deposit in the conduit, the data being generated by a deposition identification model, wherein the deposition identification model utilizes the signal as an input;
   generating a treatment plan based at least in part on the data representing the deposit; and
   applying a chemical additive to the conduit based at least in part on the treatment plan.

2. The method of claim 1 wherein measuring the signal comprises measuring the signal with a pressure transducer, microphone, hydrophone, or any combination thereof.

3. The method of claim 1 wherein generating data representing the deposit further comprises performing a calibration calculation and using an output of the calibration calculation in the deposition identification model.

4. The method of claim 3 wherein the calibration calculation confirms at least one of acoustic velocity, viscosity, or density.

5. The method of claim 1 wherein the treatment plan comprises an identity and a pump rate of the chemical additive, the chemical additive being operable to treat the deposit, wherein the identity and the pump rate of the chemical additive are determined by the data representing the deposit, predicted future deposits, a regression model of historical deposits, well maturity, forecasts of expected asphaltene, paraffin, scale, or hydrate content of produced fluids based on well age.

6. The method of claim 5 wherein the deposit is at least one of asphaltene, paraffin, hydrate, or scale.

7. The method of claim 1 further comprising:
   performing an integrated analysis of at least one of environmental characteristics, fluid characteristics, or deposition characteristics to generate integrated analysis data; and
   comparing the data representing the deposit to a regression model of historical deposits to generate a historical comparison data.

8. The method of claim 7 wherein generating the treatment plan is further based at least in part on the integrated analysis data and historical comparison data.

9. The method of claim 1 further comprising:
   determining an effectiveness of the treatment plan; and
   updating the treatment plan based at least in part on the effectiveness of the treatment plan.

10. The method of claim 1 wherein applying the chemical additive comprises transmitting the treatment plan to a treatment unit, the treatment unit comprising a control system operable to implement the treatment plan by controlling a pump fluidically connected to the chemical additive.

11. A non-transitory computer readable medium having data stored therein representing a software executable by a computer, the software executable including instructions comprising:
    instructions to accept a computer file representing acoustical or pressure signals;
    instructions to generate deposition data representing a deposit, the deposition data being generated by a deposition identification model wherein the deposition identification model utilizes the acoustical or pressure signals as an input; and
    instructions to generate a treatment plan based at least in part on the deposition data representing the deposit.

12. The non-transitory computer readable medium of claim 11 wherein the instructions further comprise:
    instructions to perform a calibration calculation and using an output of the calibration calculation in the deposition identification model.

13. The non-transitory computer readable medium of claim 12 wherein the calibration calculation confirms at least one of acoustic velocity, viscosity, or density.

14. The non-transitory computer readable medium of claim 11 wherein the instructions to generate a treatment plan comprise:
    instructions to select at least one chemical additive and a pump rate thereof based at least in part on the deposition data representing the deposit, wherein the chemical additive and the pump rate of the chemical additive are determined by the data representing the deposit, predicted future deposits, a regression model of historical deposits, well maturity, forecasts of expected asphaltene, paraffin, scale, or hydrate content of produced fluids based on well age.

15. The non-transitory computer readable medium of claim 14 wherein the instructions to generate a treatment plan further comprise:
instructions to perform an integrated analysis of at least one of environmental characteristics, fluid characteristics, or deposition characteristics to generate integrated analysis data, wherein the instructions to select at least one chemical additive and the pump rate thereof is further based at least in part on a result of the integrated analysis.

16. The non-transitory computer readable medium of claim 11 further comprising:
instructions to transmit the treatment plan to a treatment unit.

17. A system comprising:
an acoustical or pressure signal generator configured to generate an acoustical or pressure signal;
an acoustical or pressure signal receiver configured to receive the acoustical or pressure signal and generate a signal output;
a signal analysis unit configured to accept the signal output and generate data representing a deposit;
a treatment analysis unit configured to accept the data representing the deposit as an input and generate a treatment plan, the treatment plan comprising at least one chemical additive and a flow rate thereof; and
a treatment unit configured to accept the treatment plan as an input.

18. The system of claim 17 wherein the treatment analysis unit configured to generate the treatment plan based at least in part on historical deposition trends, an integrated analysis of environmental characteristics, fluid characteristics, or deposition characteristics, and the data representing the deposit.

19. The system of claim 17 wherein the treatment unit comprises:
a pump fluidically coupled to the chemical additive; and
a control system operable to control the pump, wherein the control system is configured to accept the treatment plan as an input and control the pump based at least in part on the treatment plan.

* * * * *